United States Patent
Manalad et al.

(10) Patent No.: US 12,181,422 B2
(45) Date of Patent: Dec. 31, 2024

(54) PROBABILISTIC IMAGE ANALYSIS

(71) Applicant: Rapiscan Holdings, Inc., Hawthorne (CA)

(72) Inventors: James Manalad, St-Laurent (CA); Philippe Desjeans-Gauthier, St-Laurent (CA); Simon Archambault, St-Laurent (FR); William Awad, St-Laurent (FR); Francois Brillon, St-Laurent (FR)

(73) Assignee: Rapiscan Holdings, Inc., Hawthorne, CA (US)

( * ) Notice: Subject to any disclaimer, the term of this patent is extended or adjusted under 35 U.S.C. 154(b) by 311 days.

(21) Appl. No.: 17/642,381

(22) PCT Filed: Sep. 15, 2020

(86) PCT No.: PCT/CA2020/051239
§ 371 (c)(1),
(2) Date: Mar. 11, 2022

(87) PCT Pub. No.: WO2021/051191
PCT Pub. Date: Mar. 25, 2021

(65) Prior Publication Data
US 2022/0323030 A1  Oct. 13, 2022

Related U.S. Application Data

(60) Provisional application No. 62/900,713, filed on Sep. 16, 2019.

(51) Int. Cl.
G01N 23/04 (2018.01)
A61B 6/00 (2024.01)
(Continued)

(52) U.S. Cl.
CPC .......... *G01N 23/04* (2013.01); *A61B 6/4241* (2013.01); *A61B 6/482* (2013.01); *G06V 10/56* (2022.01); *G06V 10/82* (2022.01); *A61B 6/5205* (2013.01)

(58) Field of Classification Search
CPC ...... G01N 23/04; G01N 23/083; G01N 21/88; G01N 33/02; G01N 2223/618;
(Continued)

(56) References Cited

U.S. PATENT DOCUMENTS

| 2,831,123 A | 4/1958 | Daly |
| 3,239,706 A | 3/1966 | Farrell |

(Continued)

FOREIGN PATENT DOCUMENTS

| CA | 1301371 | 5/1992 |
| CA | 2163884 | 12/1994 |

(Continued)

OTHER PUBLICATIONS

International Search Report and Written Opinion for International Application No. PCT/CA2020/051239, dated Dec. 16, 2020, (17 pages).

(Continued)

*Primary Examiner* — Irakli Kiknadze
(74) *Attorney, Agent, or Firm* — Novel IP

(57) ABSTRACT

A method for detecting at least one object of interest in at least one raw data x-ray image includes the steps of emitting an incident x-ray radiation beam through a scanning volume having an object therein, detecting x-ray signals transmitted through at least one of the scanning volume and the object, deriving the at least one raw data x-ray image from the detected x-ray signals, inputting the raw data x-ray image, expressed according to an attenuation scale, into a neural network, for each pixel in the raw data x-ray image, out-
(Continued)

putting from the neural network a probability value assigned to that pixel, and, classifying each pixel in the raw data x-ray image into a first classification if the probability value associated with the pixel exceeds a predetermined threshold probability value and in a second classification if the probability value associated with the pixel is below the predetermined threshold probability value.

17 Claims, 5 Drawing Sheets

(51) Int. Cl.
  *A61B 6/42* (2024.01)
  *G06V 10/56* (2022.01)
  *G06V 10/82* (2022.01)

(58) Field of Classification Search
  CPC ............. G01N 23/20083; G01N 23/10; G01N 23/046; G06V 10/82; G06V 10/56; G06V 10/25; G06V 10/24; G06V 10/84; G06V 10/454; G06V 10/54; G06V 20/00; G06V 20/68; A61B 6/482; A61B 6/4241; A61B 6/5205; G06F 18/24137; G06F 18/24133; G06N 3/045; G06N 3/084; G06N 3/02; G06N 3/08; G06N 3/0454; G06T 7/37; G06T 7/00; G06T 7/0004; G06T 7/40; G06T 2207/10116; G06T 2207/20081; G06T 2207/20084; G06T 2207/30128; G06T 7/001; G06T 7/12; G06T 7/143; G06T 7/187; G06K 9/00624; G06K 9/4628; G06K 9/6272; G06K 2209/17; G06K 9/4652; G06K 9/627; G01V 5/0016; G01V 5/226; G01V 5/222; G01V 5/22; G01T 1/247; G01T 1/246; G01T 1/2985
  USPC ..................................................... 378/57, 62
  See application file for complete search history.

(56) References Cited

U.S. PATENT DOCUMENTS

| | | |
|---|---|---|
| 3,766,387 A | 10/1973 | Heffan |
| 3,768,645 A | 10/1973 | Conway |
| 3,784,837 A | 1/1974 | Holmstrom |
| 4,020,346 A | 4/1977 | Dennis |
| 4,047,035 A | 9/1977 | Dennhoven |
| 4,057,725 A | 11/1977 | Wagner |
| 4,105,922 A | 8/1978 | Lambert |
| 4,139,771 A | 2/1979 | Dennhoven |
| 4,210,811 A | 7/1980 | Dennhoven |
| 4,216,499 A | 8/1980 | Dennhoven |
| 4,228,353 A | 10/1980 | Johnson |
| 4,259,721 A | 3/1981 | Kuznia |
| 4,266,425 A | 5/1981 | Allport |
| 4,274,005 A | 6/1981 | Yamamura |
| 4,352,021 A | 9/1982 | Boyd |
| 4,366,382 A | 12/1982 | Kotowski |
| 4,430,568 A | 2/1984 | Yoshida |
| 4,566,113 A | 1/1986 | Doenges |
| 4,593,355 A | 6/1986 | Chase |
| 4,599,740 A | 7/1986 | Cable |
| 4,618,978 A | 10/1986 | Cosman |
| 4,641,330 A | 2/1987 | Herwig |
| 4,675,890 A | 6/1987 | Plessis |
| 4,736,401 A | 4/1988 | Donges |
| 4,754,469 A | 6/1988 | Harding |
| 4,788,704 A | 11/1988 | Donges |
| 4,789,930 A | 12/1988 | Sones |
| 4,825,454 A | 4/1989 | Annis |
| 4,868,856 A | 9/1989 | Frith |
| 4,872,188 A | 10/1989 | Lauro |
| 4,884,289 A | 11/1989 | Glockmann |
| 4,887,604 A | 12/1989 | Shefer |
| 4,956,856 A | 9/1990 | Harding |
| 4,979,202 A | 12/1990 | Siczek |
| 4,987,584 A | 1/1991 | Doenges |
| 4,991,189 A | 2/1991 | Boomgaarden |
| 5,007,072 A | 4/1991 | Jenkins |
| 5,008,911 A | 4/1991 | Harding |
| 5,022,062 A | 6/1991 | Annis |
| 5,033,106 A | 7/1991 | Kita |
| 5,044,002 A | 8/1991 | Stein |
| 5,065,418 A | 11/1991 | Bermbach |
| 5,091,924 A | 2/1992 | Bermbach |
| 5,098,640 A | 3/1992 | Gozani |
| 5,164,590 A | 11/1992 | Coles |
| 5,179,581 A | 1/1993 | Annis |
| 5,181,234 A | 1/1993 | Smith |
| 5,182,764 A | 1/1993 | Peschmann |
| 5,224,144 A | 6/1993 | Annis |
| 5,237,598 A | 8/1993 | Albert |
| 5,247,561 A | 9/1993 | Kotowski |
| 5,253,283 A | 10/1993 | Annis |
| 5,263,075 A | 11/1993 | McGann |
| 5,265,144 A | 11/1993 | Harding |
| 5,272,627 A | 12/1993 | Maschhoff |
| 5,313,511 A | 5/1994 | Annis |
| 5,319,547 A | 6/1994 | Krug |
| 5,367,552 A | 11/1994 | Peschmann |
| 5,379,334 A | 1/1995 | Zimmer |
| 5,410,156 A | 4/1995 | Miller |
| 5,420,905 A | 5/1995 | Bertozzi |
| 5,467,377 A | 11/1995 | Dawson |
| 5,490,196 A | 2/1996 | Rudich |
| 5,490,218 A | 2/1996 | Krug |
| 5,493,596 A | 2/1996 | Annis |
| 5,524,133 A | 6/1996 | Neale |
| 5,532,492 A | 7/1996 | He |
| 5,541,856 A | 7/1996 | Hammermeister |
| 5,557,108 A | 9/1996 | Tumer |
| 5,600,303 A | 2/1997 | Husseiny |
| 5,600,700 A | 2/1997 | Krug |
| 5,606,167 A | 2/1997 | Miller |
| 5,633,907 A | 5/1997 | Gravelle |
| 5,638,420 A | 6/1997 | Armistead |
| 5,642,393 A | 6/1997 | Krug |
| 5,642,394 A | 6/1997 | Rothschild |
| 5,661,774 A | 8/1997 | Gordon |
| 5,666,393 A | 9/1997 | Annis |
| 5,687,210 A | 11/1997 | Maitrejean |
| 5,692,028 A | 11/1997 | Geus |
| 5,712,926 A | 1/1998 | Eberhard |
| 5,745,543 A | 4/1998 | De Bokx |
| 5,751,837 A | 5/1998 | Watanabe |
| 5,764,683 A | 6/1998 | Swift |
| 5,768,334 A | 6/1998 | Maitrejean |
| 5,787,145 A | 7/1998 | Geus |
| 5,796,802 A | 8/1998 | Gordon |
| 5,805,660 A | 9/1998 | Perion |
| 5,818,897 A | 10/1998 | Gordon |
| 5,838,758 A | 11/1998 | Krug |
| 5,838,759 A | 11/1998 | Armistead |
| 5,859,891 A | 1/1999 | Hibbard |
| 5,872,829 A | 2/1999 | Wischmann |
| 5,881,122 A | 3/1999 | Crawford |
| 5,887,047 A | 3/1999 | Bailey |
| 5,901,198 A | 5/1999 | Crawford |
| 5,903,623 A | 5/1999 | Swift |
| 5,905,806 A | 5/1999 | Eberhard |
| 5,909,477 A | 6/1999 | Crawford |
| 5,910,973 A | 6/1999 | Grodzins |
| 5,930,326 A | 7/1999 | Rothschild |
| 5,940,468 A | 8/1999 | Huang |
| 5,974,111 A | 10/1999 | Krug |
| 5,982,843 A | 11/1999 | Bailey |
| 6,005,912 A | 12/1999 | Oclepppo |
| 6,018,562 A | 1/2000 | Willson |
| 6,021,174 A | 2/2000 | Campbell |
| 6,026,143 A | 2/2000 | Simanovsky |

(56) References Cited

U.S. PATENT DOCUMENTS

| | | | |
|---|---|---|---|
| 6,026,171 A | 2/2000 | Hiraoglu |
| 6,031,890 A | 2/2000 | Bermbach |
| 6,035,014 A | 3/2000 | Hiraoglu |
| 6,037,597 A | 3/2000 | Karavolos |
| 6,054,712 A | 4/2000 | Komardin |
| 6,058,158 A | 5/2000 | Eiler |
| 6,058,159 A | 5/2000 | Conway |
| 6,067,344 A | 5/2000 | Grodzins |
| 6,067,366 A | 5/2000 | Simanovsky |
| 6,075,871 A | 6/2000 | Simanovsky |
| 6,076,400 A | 6/2000 | Bechwati |
| 6,078,642 A | 6/2000 | Simanovsky |
| 6,081,580 A | 6/2000 | Grodzins |
| 6,088,423 A | 7/2000 | Krug |
| 6,091,795 A | 7/2000 | Schafer |
| 6,094,472 A | 7/2000 | Smith |
| 6,108,396 A | 8/2000 | Bechwati |
| 6,111,974 A | 8/2000 | Hiraoglu |
| 6,118,850 A | 9/2000 | Mayo |
| 6,118,852 A | 9/2000 | Rogers |
| 6,122,343 A | 9/2000 | Pidcock |
| 6,128,365 A | 10/2000 | Bechwati |
| 6,151,381 A | 11/2000 | Grodzins |
| 6,163,591 A | 12/2000 | Benjamin |
| 6,181,765 B1 | 1/2001 | Sribar |
| 6,183,139 B1 | 2/2001 | Solomon |
| 6,185,272 B1 | 2/2001 | Hiraoglu |
| 6,188,745 B1 | 2/2001 | Gordon |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,195,444 B1 | 2/2001 | Simanovsky |
| 6,198,795 B1 | 3/2001 | Naumann |
| 6,216,540 B1 | 4/2001 | Nelson |
| 6,218,943 B1 | 4/2001 | Ellenbogexn |
| 6,236,709 B1 | 5/2001 | Perry |
| 6,249,567 B1 | 6/2001 | Rothschild |
| 6,252,929 B1 | 6/2001 | Swift |
| 6,256,369 B1 | 7/2001 | Lai |
| 6,256,404 B1 | 7/2001 | Gordon |
| 6,269,142 B1 | 7/2001 | Smith |
| 6,272,230 B1 | 8/2001 | Hiraoglu |
| 6,278,115 B1 | 8/2001 | Annis |
| 6,282,260 B1 | 8/2001 | Grodzins |
| 6,292,533 B1 | 9/2001 | Swift |
| 6,301,326 B2 | 10/2001 | Bjorkholm |
| 6,304,629 B1 | 10/2001 | Conway |
| 6,317,509 B1 | 11/2001 | Simanovsky |
| 6,320,933 B1 | 11/2001 | Grodzins |
| 6,324,249 B1 | 11/2001 | Fazzio |
| 6,345,113 B1 | 2/2002 | Crawford |
| 6,356,620 B1 | 3/2002 | Rothschild |
| 6,379,043 B1 | 4/2002 | Zylka |
| 6,418,189 B1 | 7/2002 | Schafer |
| 6,421,420 B1 | 7/2002 | Grodzins |
| 6,424,695 B1 | 7/2002 | Grodzins |
| 6,429,578 B1 | 8/2002 | Danielsson |
| 6,430,255 B2 | 8/2002 | Fenkart |
| 6,434,219 B1 | 8/2002 | Rothschild |
| 6,435,715 B1 | 8/2002 | Betz |
| 6,442,233 B1 | 8/2002 | Grodzins |
| 6,445,765 B1 | 9/2002 | Frank |
| 6,453,003 B1 | 9/2002 | Springer |
| 6,453,007 B2 | 9/2002 | Adams |
| 6,456,684 B1 | 9/2002 | Mun |
| 6,459,755 B1 | 10/2002 | Li |
| 6,459,761 B1 | 10/2002 | Grodzins |
| 6,459,764 B1 | 10/2002 | Chalmers |
| 6,473,487 B1 | 10/2002 | Le |
| RE37,899 E | 11/2002 | Grodzins |
| 6,483,894 B2 | 11/2002 | Hartick |
| 6,490,477 B1 | 12/2002 | Zylka |
| 6,507,025 B1 | 1/2003 | Verbinski |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,546,072 B1 | 4/2003 | Chalmers |
| 6,552,346 B2 | 4/2003 | Verbinski |
| 6,556,653 B2 | 4/2003 | Hussein |
| 6,563,903 B2 | 5/2003 | Kang |
| 6,563,906 B2 | 5/2003 | Hussein |
| 6,580,778 B2 | 6/2003 | Meder |
| 6,584,170 B2 | 6/2003 | Aust |
| 6,590,956 B2 | 7/2003 | Fenkart |
| 6,597,760 B2 | 7/2003 | Beneke |
| 6,606,516 B2 | 8/2003 | Levine |
| 6,618,466 B1 | 9/2003 | Ning |
| 6,621,888 B2 | 9/2003 | Grodzins |
| 6,628,745 B1 | 9/2003 | Annis |
| 6,636,581 B2 | 10/2003 | Sorenson |
| 6,647,091 B2 | 11/2003 | Fenkart |
| 6,647,094 B2 | 11/2003 | Harding |
| 6,647,095 B2 | 11/2003 | Hsieh |
| 6,653,588 B1 | 11/2003 | Gillard-Hickman |
| 6,658,087 B2 | 12/2003 | Chalmers |
| 6,663,280 B2 | 12/2003 | Doenges |
| 6,665,373 B1 | 12/2003 | Kotowski |
| 6,665,433 B2 | 12/2003 | Roder |
| 6,687,333 B2 | 2/2004 | Carroll |
| 6,690,766 B2 | 2/2004 | Kresse |
| 6,707,879 B2 | 3/2004 | McClelland |
| 6,715,533 B2 | 4/2004 | Kresse |
| 6,721,387 B1 | 4/2004 | Naidu |
| 6,735,271 B1 | 5/2004 | Rand |
| 6,737,652 B2 | 5/2004 | Lanza |
| 6,748,043 B1 | 6/2004 | Dobbs |
| 6,754,298 B2 | 6/2004 | Fessler |
| 6,770,884 B2 | 8/2004 | Bryman |
| 6,775,348 B2 | 8/2004 | Hoffman |
| 6,785,357 B2 | 8/2004 | Bernardi |
| 6,788,761 B2 | 9/2004 | Bijjani |
| 6,798,863 B2 | 9/2004 | Sato |
| 6,812,426 B1 | 11/2004 | Kotowski |
| 6,813,374 B1 | 11/2004 | Karimi |
| 6,816,571 B2 | 11/2004 | Bijjani |
| 6,827,265 B2 | 12/2004 | Knowles |
| 6,830,185 B2 | 12/2004 | Tsikos |
| 6,837,422 B1 | 1/2005 | Meder |
| 6,837,432 B2 | 1/2005 | Tsikos |
| 6,839,403 B1 | 1/2005 | Kotowski |
| 6,856,667 B2 | 2/2005 | Ellenbogen |
| 6,859,514 B2 | 2/2005 | Hoffman |
| 6,895,072 B2 | 5/2005 | Schrock |
| 6,901,135 B2 | 5/2005 | Fox |
| 6,906,329 B2 | 6/2005 | Bryman |
| 6,907,101 B2 | 6/2005 | Hoffman |
| 6,922,455 B2 | 7/2005 | Jurczyk |
| 6,922,460 B2 | 7/2005 | Skatter |
| 6,922,461 B2 | 7/2005 | Kang |
| 6,928,137 B2 | 8/2005 | Bruder et al. |
| 6,928,141 B2 | 8/2005 | Carver |
| 6,933,504 B2 | 8/2005 | Hoffman |
| 6,934,354 B2 | 8/2005 | Hoffman |
| 6,940,071 B2 | 9/2005 | Ramsden |
| 6,944,264 B2 | 9/2005 | Bijjani |
| 6,947,517 B2 | 9/2005 | Hoffman |
| 6,950,492 B2 | 9/2005 | Besson |
| 6,950,493 B2 | 9/2005 | Besson |
| 6,952,163 B2 | 10/2005 | Huey |
| 6,953,935 B1 | 10/2005 | Hoffman |
| 6,957,913 B2 | 10/2005 | Renkart |
| 6,962,289 B2 | 11/2005 | Vatan |
| 6,968,030 B2 | 11/2005 | Hoffman |
| 6,968,034 B2 | 11/2005 | Ellenbogen |
| 6,971,577 B2 | 12/2005 | Tsikos |
| 6,973,158 B2 | 12/2005 | Besson |
| 6,975,698 B2 | 12/2005 | Katcha |
| 6,978,936 B2 | 12/2005 | Tsikos |
| 6,980,627 B2 | 12/2005 | Qiu |
| 6,990,171 B2 | 1/2006 | Toth |
| 6,990,172 B2 | 1/2006 | Toth |
| 6,991,371 B2 | 1/2006 | Georgeson |

(56) References Cited

U.S. PATENT DOCUMENTS

| | | |
|---|---|---|
| 6,993,111 B1 | 1/2006 | Annis |
| 6,996,209 B2 | 2/2006 | Marek |
| 7,010,083 B2 | 3/2006 | Hoffman |
| 7,016,459 B2 | 3/2006 | Ellenbogen |
| 7,020,241 B2 | 3/2006 | Beneke |
| 7,020,242 B2 | 3/2006 | Ellenbogen |
| 7,023,956 B2 | 4/2006 | Heaton |
| 7,023,957 B2 | 4/2006 | Bijjani |
| 7,027,553 B2 | 4/2006 | Dunham |
| 7,027,554 B2 | 4/2006 | Gaultier |
| 7,031,430 B2 | 4/2006 | Kaucic, Jr. |
| 7,031,434 B1 | 4/2006 | Saunders |
| 7,034,313 B2 | 4/2006 | Hoffman |
| 7,039,154 B1 | 5/2006 | Ellenbogen |
| 7,045,787 B1 | 5/2006 | Verbinski |
| 7,046,756 B2 | 5/2006 | Hoffman |
| 7,046,761 B2 | 5/2006 | Ellenbogen |
| 7,050,536 B1 | 5/2006 | Fenkart |
| 7,054,408 B2 | 5/2006 | Jiang |
| 7,062,009 B2 | 6/2006 | Karimi |
| 7,062,011 B1 | 6/2006 | Tybinkowski |
| 7,062,074 B1 | 6/2006 | Beneke |
| 7,064,334 B2 | 6/2006 | Hoffman |
| 7,065,175 B2 | 6/2006 | Green |
| 7,065,179 B2 | 6/2006 | Block |
| 7,068,750 B2 | 6/2006 | Toth |
| 7,068,751 B2 | 6/2006 | Toth |
| 7,072,434 B1 | 7/2006 | Tybinkowski |
| 7,076,029 B2 | 7/2006 | Toth |
| 7,078,699 B2 | 7/2006 | Seppi |
| 7,081,628 B2 | 7/2006 | Granfors |
| 7,084,404 B2 | 8/2006 | Hoffman |
| 7,087,902 B2 | 8/2006 | Wang |
| 7,088,799 B2 | 8/2006 | Hoffman |
| 7,090,133 B2 | 8/2006 | Zhu |
| 7,092,481 B2 | 8/2006 | Hoffman |
| 7,092,485 B2 | 8/2006 | Kravis |
| 7,103,137 B2 | 9/2006 | Seppi |
| 7,106,830 B2 | 9/2006 | Rosner |
| 7,110,488 B2 | 9/2006 | Katcha |
| 7,112,797 B2 | 9/2006 | Hoge |
| 7,116,749 B2 | 10/2006 | Besson |
| 7,116,751 B2 | 10/2006 | Ellenbogen |
| 7,119,553 B2 | 10/2006 | Yang |
| 7,123,681 B2 | 10/2006 | Ellenbogen |
| 7,127,027 B2 | 10/2006 | Hoffman |
| 7,130,374 B1 | 10/2006 | Jacobs |
| 7,133,491 B2 | 11/2006 | Bernardi |
| 7,136,450 B2 | 11/2006 | Ying |
| 7,136,451 B2 | 11/2006 | Naidu |
| 7,139,367 B1 | 11/2006 | Le |
| 7,139,406 B2 | 11/2006 | McClelland |
| 7,149,278 B2 | 12/2006 | Arenson |
| 7,149,339 B2 | 12/2006 | Veneruso |
| 7,155,812 B1 | 1/2007 | Peterson |
| 7,158,611 B2 | 1/2007 | Heismann |
| 7,162,005 B2 | 1/2007 | Bjorkholm |
| 7,164,747 B2 | 1/2007 | Ellenbogen |
| 7,164,750 B2 | 1/2007 | Nabors |
| 7,166,458 B2 | 1/2007 | Ballerstadt |
| 7,167,539 B1 | 1/2007 | Hoffman |
| 7,173,998 B2 | 2/2007 | Hoffman |
| 7,177,387 B2 | 2/2007 | Yasunaga |
| 7,177,391 B2 | 2/2007 | Chapin |
| 7,190,757 B2 | 3/2007 | Ying |
| 7,197,113 B1 | 3/2007 | Katcha |
| 7,197,172 B1 | 3/2007 | Naidu |
| 7,207,713 B2 | 4/2007 | Lowman |
| 7,215,731 B1 | 5/2007 | Basu |
| 7,215,738 B2 | 5/2007 | Muenchau |
| 7,218,704 B1 | 5/2007 | Adams |
| 7,221,732 B1 | 5/2007 | Annis |
| 7,224,763 B2 | 5/2007 | Naidu |
| 7,224,765 B2 | 5/2007 | Ellenbogen |
| 7,224,766 B2 | 5/2007 | Jiang |
| 7,224,769 B2 | 5/2007 | Turner |
| 7,233,640 B2 | 6/2007 | Ikhlef |
| 7,236,564 B2 | 6/2007 | Hopkins |
| 7,238,945 B2 | 7/2007 | Hoffman |
| 7,247,856 B2 | 7/2007 | Hoge |
| 7,251,310 B2 | 7/2007 | Smith |
| 7,260,170 B2 | 8/2007 | Arenson |
| 7,260,171 B1 | 8/2007 | Arenson |
| 7,260,172 B2 | 8/2007 | Arenson |
| 7,260,173 B2 | 8/2007 | Wakayama |
| 7,260,174 B2 | 8/2007 | Hoffman |
| 7,260,182 B2 | 8/2007 | Toth |
| 7,263,160 B2 | 8/2007 | Schlomka |
| 7,266,180 B1 | 9/2007 | Saunders |
| 7,272,429 B2 | 9/2007 | Walker |
| 7,274,767 B2 | 9/2007 | Clayton |
| 7,277,577 B2 | 10/2007 | Ying |
| 7,279,120 B2 | 10/2007 | Cheng |
| 7,280,631 B2 | 10/2007 | De Man |
| 7,282,727 B2 | 10/2007 | Retsky |
| 7,283,604 B2 | 10/2007 | De Man |
| 7,283,609 B2 | 10/2007 | Possin |
| 7,295,019 B2 | 11/2007 | Yang |
| 7,298,812 B2 | 11/2007 | Tkaczyk |
| 7,302,083 B2 | 11/2007 | Larson |
| 7,308,073 B2 | 12/2007 | Tkaczyk |
| 7,308,074 B2 | 12/2007 | Jiang |
| 7,308,077 B2 | 12/2007 | Bijjani |
| 7,317,195 B2 | 1/2008 | Eikman |
| 7,317,390 B2 | 1/2008 | Huey |
| 7,319,737 B2 | 1/2008 | Singh |
| 7,322,745 B2 | 1/2008 | Agrawal |
| 7,324,625 B2 | 1/2008 | Eilbert |
| 7,327,853 B2 | 2/2008 | Ying |
| 7,330,527 B2 | 2/2008 | Hoffman |
| 7,330,535 B2 | 2/2008 | Arenson |
| 7,333,589 B2 | 2/2008 | Ellenbogen |
| 7,335,887 B1 | 2/2008 | Verbinski |
| 7,336,769 B2 | 2/2008 | Arenson |
| 7,339,159 B2 | 3/2008 | Juh |
| 7,366,282 B2 | 4/2008 | Peschmann |
| 7,369,643 B2 | 5/2008 | Kotowski |
| 7,384,194 B2 | 6/2008 | Gatten |
| 7,417,440 B2 | 8/2008 | Peschmann |
| 7,453,987 B1 | 11/2008 | Richardson |
| 7,486,772 B2 | 2/2009 | Lu |
| 7,505,562 B2 | 3/2009 | Dinca |
| 7,551,718 B2 | 6/2009 | Rothschild |
| 7,555,099 B2 | 6/2009 | Rothschild |
| 7,579,845 B2 | 8/2009 | Peschmann |
| 7,606,348 B2 | 10/2009 | Foland |
| 7,609,807 B2 | 10/2009 | Leue |
| 7,634,051 B2 | 12/2009 | Robinson |
| 7,636,418 B2 | 12/2009 | Anwar |
| 7,656,995 B2 | 2/2010 | Robinson |
| 7,668,289 B2 | 2/2010 | Proksa |
| 7,672,427 B2 | 3/2010 | Chen |
| 7,693,261 B2 | 4/2010 | Robinson |
| 7,706,507 B2 | 4/2010 | Williamson |
| 7,734,066 B2 | 6/2010 | DeLia |
| 7,796,733 B2 | 9/2010 | Hughes |
| 7,831,012 B2 | 11/2010 | Foland |
| 7,856,081 B2 | 12/2010 | Peschmann |
| 7,864,920 B2 | 1/2011 | Rothschild |
| 7,873,201 B2 | 1/2011 | Eilbert |
| 7,876,879 B2 | 1/2011 | Morton |
| 7,924,979 B2 | 4/2011 | Rothschild |
| 7,945,017 B2 | 5/2011 | Chen |
| 7,965,816 B2 | 6/2011 | Kravis |
| 7,995,707 B2 | 8/2011 | Rothschild |
| 8,009,799 B2 | 8/2011 | Doyle |
| 8,009,800 B2 | 8/2011 | Doyle |
| 8,014,493 B2 | 9/2011 | Roux |
| 8,031,903 B2 | 10/2011 | Paresi |
| 8,098,794 B1 | 1/2012 | Fernandez |
| 8,116,428 B2 | 2/2012 | Gudmundson |
| 8,135,110 B2 | 3/2012 | Morton |
| 8,135,112 B2 | 3/2012 | Hughes |
| 8,138,770 B2 | 3/2012 | Peschmann |

(56) References Cited

U.S. PATENT DOCUMENTS

| | | |
|---|---|---|
| D658,294 S | 4/2012 | Awad |
| 8,189,889 B2 | 5/2012 | Pearlstein |
| 8,204,173 B2 | 6/2012 | Betcke |
| 8,223,919 B2 | 7/2012 | Morton |
| 8,233,588 B2 | 7/2012 | Gibson |
| 8,284,896 B2 | 10/2012 | Singh |
| 8,311,309 B2 | 11/2012 | Siedenburg |
| 8,320,523 B2 | 11/2012 | Zhang |
| 8,401,270 B2 | 3/2013 | Eilbert |
| 8,428,217 B2 | 4/2013 | Peschmann |
| 8,442,186 B2 | 5/2013 | Rothschild |
| 8,478,016 B2 | 7/2013 | Robinson |
| 8,503,606 B2 | 8/2013 | Rothschild |
| 8,515,010 B1 | 8/2013 | Hurd |
| 8,537,968 B2 | 9/2013 | Radley |
| 8,559,592 B2 | 10/2013 | Betcke |
| 8,633,823 B2 | 1/2014 | Armistead, Jr. |
| 8,674,706 B2 | 3/2014 | Peschmann |
| 8,724,774 B2 | 5/2014 | Langeveld |
| 8,750,454 B2 | 6/2014 | Gozani |
| 8,774,357 B2 | 7/2014 | Morton |
| 8,774,362 B2 | 7/2014 | Hughes |
| 8,781,066 B2 | 7/2014 | Gudmundson |
| 8,804,899 B2 | 8/2014 | Morton |
| 8,831,331 B2 | 9/2014 | Gudmundson |
| 8,842,808 B2 | 9/2014 | Rothschild |
| 8,861,684 B2 | 10/2014 | Al-Kofahi |
| 8,867,816 B2 | 10/2014 | Bouchard |
| 8,879,791 B2 | 11/2014 | Drouin |
| 8,885,794 B2 | 11/2014 | Morton |
| 8,903,046 B2 | 12/2014 | Morton |
| 8,958,526 B2 | 2/2015 | Morton |
| 9,042,511 B2 | 5/2015 | Peschmann |
| 9,099,279 B2 | 8/2015 | Rommel |
| 9,111,331 B2 | 8/2015 | Parikh |
| 9,113,839 B2 | 8/2015 | Morton |
| 9,170,212 B2 | 10/2015 | Bouchard |
| 9,183,647 B2 | 11/2015 | Morton |
| 9,189,846 B2 | 11/2015 | Wismuller |
| 9,194,975 B2 | 11/2015 | Drouin |
| 9,196,082 B2 | 11/2015 | Pearlstein |
| 9,268,058 B2 | 2/2016 | Peschmann |
| 9,311,277 B2 | 4/2016 | Rinkel |
| 9,404,875 B2 | 8/2016 | Langeveld |
| 9,417,060 B1 | 8/2016 | Schubert |
| 9,466,456 B2 | 10/2016 | Rommel |
| 9,535,019 B1 | 1/2017 | Rothschild |
| 9,632,205 B2 | 4/2017 | Morton |
| 9,681,851 B2 | 6/2017 | Rohler |
| 9,733,385 B2 | 8/2017 | Franco |
| 9,746,431 B2 | 8/2017 | Grader |
| 9,747,705 B2 | 8/2017 | Morton |
| 9,772,426 B2 | 9/2017 | Armistead, Jr. |
| 9,823,383 B2 | 11/2017 | Hanley |
| 9,880,314 B2 | 1/2018 | Pfander |
| 9,989,508 B2 | 6/2018 | Awad |
| 9,996,890 B1 | 6/2018 | Cinnamon |
| 10,089,956 B2 | 10/2018 | Awad et al. |
| 10,168,445 B2 | 1/2019 | Morton |
| 10,180,483 B2 | 1/2019 | Holdsworth |
| 10,210,631 B1 | 2/2019 | Cinnamon |
| 10,254,436 B2 | 4/2019 | Awad |
| 10,295,483 B2 | 5/2019 | Morton |
| 10,302,807 B2 | 5/2019 | Yu |
| 10,366,293 B1 | 7/2019 | Faviero |
| 10,386,532 B2 | 8/2019 | Morton |
| 10,408,967 B2 | 9/2019 | Morton |
| 10,452,959 B1 | 10/2019 | Gautam |
| 10,453,223 B2 | 10/2019 | Cinnamon |
| 10,504,261 B2 | 12/2019 | Cinnamon |
| 10,510,319 B2 | 12/2019 | Awad |
| 10,555,716 B2 | 2/2020 | Rohler |
| 10,557,911 B2 | 2/2020 | Holdsworth |
| 10,572,963 B1 | 2/2020 | Cinnamon |
| 10,598,812 B2 | 3/2020 | Franco |
| 10,650,783 B2 | 5/2020 | Awad |
| 10,706,335 B2 | 7/2020 | Gautam |
| 10,768,338 B2 | 9/2020 | Yu |
| 10,782,440 B2 | 9/2020 | Hanley |
| 10,795,047 B2 | 10/2020 | St-Aubin |
| 10,795,048 B2 | 10/2020 | St-Aubin |
| 10,795,049 B2 | 10/2020 | St-Aubin |
| 10,809,414 B2 | 10/2020 | St-Aubin |
| 10,901,113 B2 | 1/2021 | Morton |
| 10,901,114 B2 | 1/2021 | St-Aubin |
| 11,010,605 B2 | 5/2021 | Nord |
| 11,073,486 B2 | 7/2021 | Siegrist |
| 11,116,471 B2 | 9/2021 | Rohler |
| 11,263,499 B2 | 3/2022 | Gautam |
| 11,275,194 B2 | 3/2022 | Morton |
| 11,276,213 B2 | 3/2022 | Cinnamon |
| 11,287,391 B2 | 3/2022 | Yu |
| 11,307,325 B2 | 4/2022 | Morton |
| 11,423,592 B2 | 8/2022 | Cinnamon |
| 11,478,214 B2 | 10/2022 | Siewerdsen |
| 11,561,320 B2 | 1/2023 | Morton |
| 11,790,575 B2 | 10/2023 | Cinnamon |
| 11,822,041 B2 | 11/2023 | Morton |
| 2001/0014137 A1 | 8/2001 | Bjorkholm |
| 2001/0022346 A1 | 9/2001 | Katagami |
| 2002/0031202 A1 | 3/2002 | Callerame |
| 2002/0094064 A1 | 7/2002 | Zhou |
| 2002/0176531 A1 | 11/2002 | McClelland |
| 2003/0031352 A1 | 2/2003 | Nelson |
| 2003/0085348 A1 | 5/2003 | Megerle |
| 2004/0091078 A1 | 5/2004 | Ambrefe |
| 2004/0120454 A1 | 6/2004 | Ellenbogen |
| 2004/0141584 A1 | 7/2004 | Bernardi |
| 2004/0179643 A1 | 9/2004 | Gregerson |
| 2004/0213378 A1 | 10/2004 | Zhou |
| 2004/0252807 A1 | 12/2004 | Skatter |
| 2004/0258305 A1 | 12/2004 | Burnham |
| 2005/0008126 A1 | 1/2005 | Juh |
| 2005/0025280 A1 | 2/2005 | Schulte |
| 2005/0031075 A1 | 2/2005 | Hopkins |
| 2005/0053189 A1 | 3/2005 | Gohno |
| 2005/0058242 A1* | 3/2005 | Peschmann ............... G01V 5/22 378/57 |
| 2005/0105682 A1 | 5/2005 | Heumann |
| 2005/0111610 A1 | 5/2005 | De Man |
| 2005/0117700 A1 | 6/2005 | Peschmann |
| 2005/0157925 A1 | 7/2005 | Lorenz |
| 2005/0180542 A1 | 8/2005 | Leue |
| 2005/0281390 A1 | 12/2005 | Johnson |
| 2006/0018428 A1 | 1/2006 | Li |
| 2006/0098866 A1 | 5/2006 | Whitson |
| 2006/0113163 A1 | 6/2006 | Hu |
| 2006/0273259 A1 | 12/2006 | Li |
| 2007/0003003 A1 | 1/2007 | Seppi |
| 2007/0003009 A1 | 1/2007 | Gray |
| 2007/0096030 A1 | 5/2007 | Li |
| 2007/0110215 A1 | 5/2007 | Hu |
| 2007/0116177 A1 | 5/2007 | Chen |
| 2007/0132580 A1 | 6/2007 | Ambrefe, Jr. |
| 2007/0133740 A1 | 6/2007 | Kang |
| 2007/0133742 A1 | 6/2007 | Gatten |
| 2007/0172129 A1 | 7/2007 | Tortora |
| 2007/0183568 A1 | 8/2007 | Kang |
| 2007/0235652 A1 | 10/2007 | Smith |
| 2007/0280502 A1 | 12/2007 | Paresi |
| 2008/0025470 A1 | 1/2008 | Streyl |
| 2008/0063140 A1 | 3/2008 | Awad |
| 2008/0232668 A1 | 9/2008 | Kitamura |
| 2009/0010386 A1 | 1/2009 | Peschmann |
| 2009/0060135 A1 | 3/2009 | Morton |
| 2009/0196396 A1 | 8/2009 | Doyle |
| 2009/0285353 A1 | 11/2009 | Ellenbogen |
| 2010/0002834 A1 | 1/2010 | Gudmundson |
| 2010/0027741 A1 | 2/2010 | Doyle |
| 2010/0086185 A1 | 4/2010 | Weiss |
| 2010/0098218 A1 | 4/2010 | Vermilyea |
| 2010/0207741 A1 | 8/2010 | Gudmundson |
| 2010/0208972 A1 | 8/2010 | Bouchard |
| 2010/0223016 A1 | 9/2010 | Gibson |

(56) References Cited

U.S. PATENT DOCUMENTS

| | | |
|---|---|---|
| 2010/0277312 A1 | 11/2010 | Edic |
| 2010/0295689 A1 | 11/2010 | Armistead, Jr. |
| 2010/0302034 A1 | 12/2010 | Clements |
| 2011/0007870 A1 | 1/2011 | Roux |
| 2011/0019797 A1 | 1/2011 | Morton |
| 2011/0033118 A1 | 2/2011 | Yildiz |
| 2011/0172972 A1 | 7/2011 | Gudmundson |
| 2011/0228896 A1 | 9/2011 | Peschmann |
| 2011/0235777 A1 | 9/2011 | Gozani |
| 2012/0069964 A1 | 3/2012 | Scholling |
| 2012/0093367 A1 | 4/2012 | Gudmundson |
| 2012/0140879 A1 | 6/2012 | Gudmundson |
| 2012/0230463 A1 | 9/2012 | Morton |
| 2012/0275646 A1 | 11/2012 | Drouin |
| 2013/0034268 A1 | 2/2013 | Perron |
| 2013/0085788 A1 | 4/2013 | Rowlan |
| 2013/0114788 A1 | 5/2013 | Crass |
| 2013/0163811 A1 | 6/2013 | Oelke |
| 2013/0251098 A1* | 9/2013 | Morton .......... H01J 35/045 378/10 |
| 2013/0292574 A1 | 11/2013 | Levene |
| 2013/0294574 A1 | 11/2013 | Peschmann |
| 2013/0301794 A1 | 11/2013 | Grader |
| 2013/0336447 A1 | 12/2013 | Morton |
| 2014/0072108 A1 | 3/2014 | Rohler |
| 2014/0185923 A1 | 7/2014 | Chen |
| 2014/0205059 A1 | 7/2014 | Sharpless |
| 2014/0211917 A1 | 7/2014 | Chen |
| 2014/0211980 A1 | 7/2014 | Bouchard |
| 2014/0222385 A1 | 8/2014 | Muenster |
| 2014/0241495 A1 | 8/2014 | Gudmundson |
| 2014/0249536 A1 | 9/2014 | Jajeh |
| 2015/0021342 A1 | 1/2015 | Crass |
| 2015/0186732 A1 | 7/2015 | Perron |
| 2015/0268016 A1 | 9/2015 | Eshetu |
| 2015/0282781 A1 | 10/2015 | Rohler |
| 2015/0355117 A1 | 12/2015 | Morton |
| 2016/0025888 A1 | 1/2016 | Peschmann |
| 2016/0252647 A1 | 9/2016 | Awad |
| 2016/0260412 A1 | 9/2016 | Awad |
| 2017/0103513 A1 | 4/2017 | Heilmann |
| 2017/0184737 A1 | 6/2017 | Dujmic |
| 2017/0184756 A1 | 6/2017 | Miao |
| 2017/0236232 A1 | 8/2017 | Morton |
| 2017/0242148 A1* | 8/2017 | Yu .......... G01V 5/22 |
| 2017/0309043 A1 | 10/2017 | Li |
| 2017/0319169 A1 | 11/2017 | Rohler |
| 2017/0328844 A1 | 11/2017 | Li |
| 2017/0371010 A1 | 12/2017 | Shanbhag |
| 2018/0106733 A1 | 4/2018 | Li |
| 2018/0162584 A1 | 6/2018 | Tauber |
| 2019/0003989 A1 | 1/2019 | Miyazaki |
| 2019/0219729 A1 | 7/2019 | St-Aubin |
| 2019/0346379 A1 | 11/2019 | Awad |
| 2019/0346381 A1 | 11/2019 | Awad |
| 2020/0085404 A1 | 3/2020 | Siewerdsen |
| 2020/0103548 A1 | 4/2020 | Yu |
| 2020/0110043 A1 | 4/2020 | Marín |
| 2020/0146648 A1 | 5/2020 | Rohler |
| 2020/0158909 A1 | 5/2020 | Morton |
| 2020/0211186 A1* | 7/2020 | Gong .......... A61B 5/0033 |
| 2020/0249179 A1 | 8/2020 | Yamakawa |
| 2020/0348247 A1 | 11/2020 | Bur |
| 2020/0355631 A1 | 11/2020 | Yu |
| 2021/0004994 A1 | 1/2021 | Kubo |
| 2021/0361254 A1 | 11/2021 | Rohler |
| 2021/0381991 A1 | 12/2021 | Desjeans-Gauthier |
| 2022/0291148 A1 | 9/2022 | Gill |

FOREIGN PATENT DOCUMENTS

| | | |
|---|---|---|
| CA | 2574402 A1 | 1/2006 |
| CA | 2744690 | 6/2009 |
| CA | 2692662 | 3/2010 |
| CA | 2697525 | 3/2010 |
| CA | 2709468 | 3/2010 |
| CA | 2690163 | 8/2011 |
| CA | 2869201 | 10/2013 |
| CN | 102175698 | 9/2011 |
| CN | 103327901 | 9/2013 |
| CN | 104165896 | 11/2014 |
| CN | 108937992 A | 12/2018 |
| CN | 116359257 A | 6/2023 |
| DE | 2729353 A1 | 1/1979 |
| EP | 0432568 | 6/1991 |
| EP | 0531993 A1 | 3/1993 |
| EP | 0584871 A1 | 3/1994 |
| EP | 0924742 A2 | 6/1999 |
| EP | 0930046 A2 | 7/1999 |
| EP | 1277439 A1 | 1/2003 |
| EP | 1374776 A1 | 1/2004 |
| FR | 2328280 A | 5/1977 |
| FR | 3037401 | 12/2016 |
| GB | 1497396 A | 1/1978 |
| GB | 1526041 A | 9/1978 |
| GB | 2015245 A | 9/1979 |
| GB | 2089109 A | 6/1982 |
| GB | 2212903 A | 8/1989 |
| GB | 2299251 | 9/1996 |
| GB | 2356453 A | 5/2001 |
| GB | 2437777 A | 11/2007 |
| JP | S57175247 A | 10/1982 |
| JP | 600015546 | 1/1985 |
| JP | 600021440 | 2/1985 |
| JP | H0479128 A | 3/1992 |
| JP | H10211196 A | 8/1998 |
| JP | 2001176408 A | 6/2001 |
| JP | 2004079128 | 3/2004 |
| JP | 3946612 | 7/2007 |
| SU | 1022236 A1 | 6/1983 |
| WO | 9423458 | 10/1994 |
| WO | 9528715 A2 | 10/1995 |
| WO | 9960387 | 11/1999 |
| WO | 03051201 A2 | 6/2003 |
| WO | 03105159 | 12/2003 |
| WO | 2004097889 A2 | 11/2004 |
| WO | 2004111625 | 12/2004 |
| WO | 2005084351 | 9/2005 |
| WO | 2006135586 | 12/2006 |
| WO | 2006137919 | 12/2006 |
| WO | 2008133765 | 11/2008 |
| WO | 2008139167 A2 | 11/2008 |
| WO | 2008157843 | 12/2008 |
| WO | 2009114928 | 9/2009 |
| WO | 2010025538 A1 | 3/2010 |
| WO | 2013149788 | 10/2013 |
| WO | 2018121444 | 7/2018 |

OTHER PUBLICATIONS

International Search Report for International Application No. PCT/CA2019/051489, dated Dec. 30, 2019, (pp. 4).

International Search Report for International Application No. PCT/CA2013/050744, dated Jun. 10, 2014, (5 pages).

K. Wells; D.A. Bradley;, "A review of X-ray explosives detection techniques for checked baggage", Applied Radiation and Isotopes., Elsevier, Oxford., GB, GB, (Jan. 12, 2012), vol. 70, No. 8, doi:10.1016/j.apradiso.2012.01.011, ISSN 0969-8043, pp. 1729-1746, XP028401820.

Richard D. R. Macdonald, "<title>Design and implementation of a dual-energy x-ray imaging system for organic material detection in an airport security application</title>", Proceedings of SPIE, SPIE, (Apr. 4, 2001), vol. 4301, doi:10.1117/12.420922, ISSN 0277786X, pp. 31-41, XP055104503.

International Search Report for corresponding International Patent Application No. PCT/CA2014/050981 dated Jan. 5, 2015, 6 pgs.

International Search Report for corresponding International Patent Application No. PCT/CA2014/051074 dated Jan. 20, 2015.

International Search Report & Written Opinion for PCT/CA2019/050616, dated Jul. 5, 2019, (15 pages).

(56) References Cited

OTHER PUBLICATIONS

International Search Report and Written for International Application No. PCT/CA2018/051673, dated Mar. 14, 2019, (8-pages).
International Search Report and Written Opinion for International Application No. PCT/CA2019/050617, dated Jul. 30, 2019, (11 pages).
International Search Report and Written Opinion for International Application No. PCT/CA2018/051674, dated Mar. 29, 2019, (8 pages).
International Search Report and Written Opinion for International Application No. PCT/CA2018/051675, dated Mar. 21, 2019, (11 pages).
International Search Report and Written Opinion for International Application No. PCT/CA2018/051676, dated Mar. 26, 2019, (7 pages).
Hurd et al (U.S. Pat. No. 8,515,010, hereafter referred to as Hurd), Ying et al ("Dual Energy Volumetric X-ray Tomographic Sensor for Luggage Screening", IEEE, SAS Feb. 2007) (Year: 2007).
International Search Report and Written Opinion for International Application No. PCT/CA2018/051677, dated Mar. 29, 2019, (8 pages).
Lehmann et al., Generalized image combinations in dual KVP digital radiography, Medical Physics, Sep. 1981, 659-667, 8-5, American Association of Physicists in Medicine.
Bond et al., ZeCalc Algorithm Details, Lawrence Livermore National Laboratory, Jan. 7, 2013, Livermore U.S.A.
Hassanpour et al (NPL "Illicit Material Detection using Dual-Energy X-ray Images", The International Arab Journal of Information Technology, vol. 13, No. 4, Jul. 2016, p. 8) (Year: 2016).
International Search Report for PCT/GB2004/001729, Aug. 12, 2004.
International Search Report for PCT/GB2004/001741, Mar. 3, 2005.
International Search Report for PCT/GB2004/001731, May 27, 2005.
International Search Report for PCT/GB2004/001732, Feb. 25, 2005.
International Search Report for PCT/GB2004/001751, Mar. 21, 2005.
International Search Report for PCT/GB2004/001747, Aug. 10, 2004, CXR Ltd.
Development of ultra-fast X-ray computed tomography scanner system, INS 98-43 6068772 A9823-8760J-016 (PHA); B9812-7510B-113 (EEA) NDN-174-0606-8771-7, Hori, K.; Fujimoto, T.; Kawanishi, K., Editor—Nalcioglu, O., Abbreviated Journal Title—1997 IEEE Nuclear Science Symposium, Conference Record (Cat. No. 97CH36135) Part No. vol. 2, 1997, pp. 1003-1008 vol. 2, 2 vol. xlviii+1761 page(s), ISBN-0 7803 4258 5.

* cited by examiner

PROBABILISTIC IMAGE ANALYSIS

CROSS-REFERENCE

The present application is a 371 national stage application of PCT Application Number PCT/CA2020/051239, titled "Probabilistic Image Analysis" and filed on Sep. 15, 2020.

TECHNICAL FIELD

The present disclosure generally relates to a system for detection of objects or materials. More particularly, the present disclosure relates to a system for detection of objects of interest using a probabilistic analysis technique.

BACKGROUND

Conventional X-ray detection usually relies on transmission signal levels or attenuation, or on the conversion of a detected x-ray transmission signals into information representing the effective atomic number, mass attenuation, density or other property or characteristic of the material being scanned provided, for example, by way of trace material detection. These values are then analyzed to detect the presence of certain materials which may be prohibited, such as drugs, or materials which may potentially be dangerous, such as explosive materials or the metal from weapons. However, the shape and the visual details of the prohibited or dangerous objects, which contain relevant information as to what the object might be, are not utilized in such an analysis.

When a trained operator looks at the image produced by an X-ray scanning machine or data provided by a trace detection device, the operator is the one to perform the analysis to assess the presence of objects or materials of interest, such as potential threats, based on their combined shape and/or composition as interpreted on visual review. Manual reviews of this type are time-consuming and are subject to human error. Accordingly, they are subject to a higher rate of false positive readings or false negative readings. Moreover, manual review does not produce data or information which can be used automatically to improve other review processes or to influence the behavior of other components operably connected to the X-ray scanning device or trace material detection device.

It is therefore desired to have a system which automatically recognizes objects or materials of interest in an inspected object, preferably in real-time or near real-time which produces useful information to be applied in future processes.

Machine learning has been applied in many ways for recognition of objects in images. Applications of machine learning have been contemplated for use in interpreting images produced by x-ray scans. As an improvement to the machine learning field, the machine learning sub-class known as "deep learning" aims to simulate human interpretation of image data. Deep learning is often characterized by the use of an algorithm or series of algorithms known as "artificial neural networks", or simply "neural networks".

In prior applications of machine learning to x-ray image analysis, observations have been represented in a variety of ways, such as a vector of each pixel intensity value, or more abstractly represented as a series of edges or regions of a particular shape, and the like. One advantage of deep learning applications to image analysis is that the neural networks may be trained in an unsupervised or semi-supervised manner to learn features and hierarchical feature extraction using efficient algorithms instead of manual acquisition of features. To simplify image analysis, a process known as "image segmentation" is used to split the input image information into segments that that represent objects or parts of objects. This allows for analysis of the images in larger components.

Some conventional applications of neural networks to analyze x-ray scan images includes identifying regions of a digital x-ray scan image which has been normalized and processed. A neural network may be used to identify one or more regions of the image that is likely to contain an object of interest. To do so, pixels may be analyzed in groups, possibly sequential groups, to identify one or more features indicative of an object of interest. Features may include, for example, edges, areas of a particular shape, concavities, convexities or any other aspect. The features identified in the pixel groups or "regions" of the image may then be input into a classification network to classify the object of interest according to one or more known objects. The classification network typically outputs one or more probabilities or "scores" that the object represented in the image belongs to a particular type or "class" of object.

Segmentation of an x-ray scan image by way of the features, such as those of shape, identified in the image is known as "instance segmentation". Instance segmentation approaches to object classification include pre-classification steps associated with feature detection because such methods are used for "recognition" of objects. Therefore, they are typically more computationally intensive and can be slower to output a classification. In applications of x-ray scanning for security purposes, it is not necessarily required to "recognize" an object of interest, but rather only to "detect" the presence of an object of interest, such as detection of an object that could be classified as "a potential threat" or "not a potential threat."

By foregoing the computationally intensive and time-consuming steps associated with object recognition, the process of detecting the presence of a potential threat may be accelerated.

SUMMARY

The present disclosure generally relates to a system for detection of objects or materials. More particularly, the present disclosure relates to a system for detection of objects of interest using a probabilistic analysis technique.

The present disclosure is in the context of probabilistic analysis of raw or unprocessed data in the form of x-ray scan images as produced by transmission x-ray scanning devices for inspection. The present disclosure would also apply to other forms data which may be extracted from an inspected object. Such other forms of data may include images provided by dual energy channels x-ray scans, multi-channel x-ray scans, trace material detection, millimeter wave scans, spectral analysis, x-ray diffraction information, x-ray backscatter images and any other means of inspection for extracting data suitable for analyzing the properties of an object subject to inspection. It should be further understood that the extracted data use for analysis may be unprocessed or processed data.

In one aspect, there is provided a method for detecting at least one object of interest in at least one raw data x-ray image. The method includes the steps of emitting an incident x-ray radiation beam through a scanning volume having an object therein; detecting x-ray signals transmitted through at least one of the scanning volume and the object; deriving the at least one raw data x-ray image from the detected x-ray signals; inputting the raw data x-ray image, expressed according to an attenuation scale, into a neural network; for each pixel in the raw data x-ray image, outputting from the neural network a probability value assigned to that pixel; and classifying each pixel in the raw data x-ray image into a first classification if the probability value associated with the pixel exceeds a predetermined threshold probability value and in a second classification if the probability value associated with the pixel is below the predetermined threshold probability value. The neural network may be a convolutional neural network. Further, the convolutional neural network may be a FC-Densenet.

After the deriving step, the step of inputting the raw data x-ray image expressed according to an attenuation scale may further comprise the steps of determining a transmittance value for each pixel in the raw data x-ray image; and determining an attenuation value from each transmittance value. The outputting step may output a probability map for each pixel in the raw data x-ray image.

The classifying step may use semantic segmentation. The first classification may indicate that the pixel is likely associated with a potential threat and the second classification may indicate that the pixel is not likely to be associated with a potential threat.

The method may further provide a colour-mapped image based on the probability map showing pixels classified in the first classification in a first colour scheme and pixels classified in the second classification in a second colour scheme. The first colour scheme and the second colour scheme may be at least one of flashing, shifting hue and shifting luma.

In another aspect, there is provided a system for detecting at least one object of interest in at least one raw data x-ray image. The method may include an x-ray emitter for emitting an incident x-ray radiation beam through a scanning volume having an object therein; at least one detector for detecting x-ray signals transmitted through at least one of the scanning volume and the object; at least one processor for deriving at least one raw data x-ray image from the detected x-ray signal; at least one processor configured to: input the raw data x-ray image, expressed according to an attenuation scale, into a neural network; output from the neural network a probability value assigned to each pixel in the raw data x-ray image; and, classify each pixel in the raw data x-ray image into a first classification if the probability value associated with the pixel exceeds a predetermined threshold probability value and in a second classification if the probability value associated with the pixel is below the predetermined threshold probability value. The neural network may be configured to classify each pixel in the raw data x-ray image by way of semantic segmentation. The neural network may be a convolutional neural network. The convolutional neural network may be a FC-Densenet.

The at least one processor may be further configured to determine a transmittance value for each pixel in the raw data x-ray image; and determine an attenuation value from each transmittance value.

The at least one processor may be configured to output a probability map for each pixel in the raw data x-ray image. The at least one processor may further be configured to provide a colour-mapped image showing pixels in the first classification in a first colour scheme and pixels in the second classification in a second colour scheme.

In another aspect, there is provided a method for determining a presence of an object of interest. The method may include the steps of: deriving a raw data image representative of at least a portion of an object; inputting the raw data image, expressed according to an attenuation scale, into a neural network; for each pixel in the raw data image, outputting from the neural network a probability value assigned to that pixel; and, classifying each pixel in the raw data image into a first classification if the probability value associated with the pixel exceeds a predetermined threshold probability value and in a second classification if the probability value associated with the pixel is below the predetermined threshold probability value.

BRIEF DESCRIPTION OF THE DRAWINGS

Exemplary non-limiting embodiments are described with reference to the accompanying drawings in which.

DETAILED DESCRIPTION

The present disclosure generally relates to a system for detection of objects or materials. More particularly, the present disclosure relates to a system for detection of objects or materials of interest using a probabilistic analysis technique.

Figure 1:
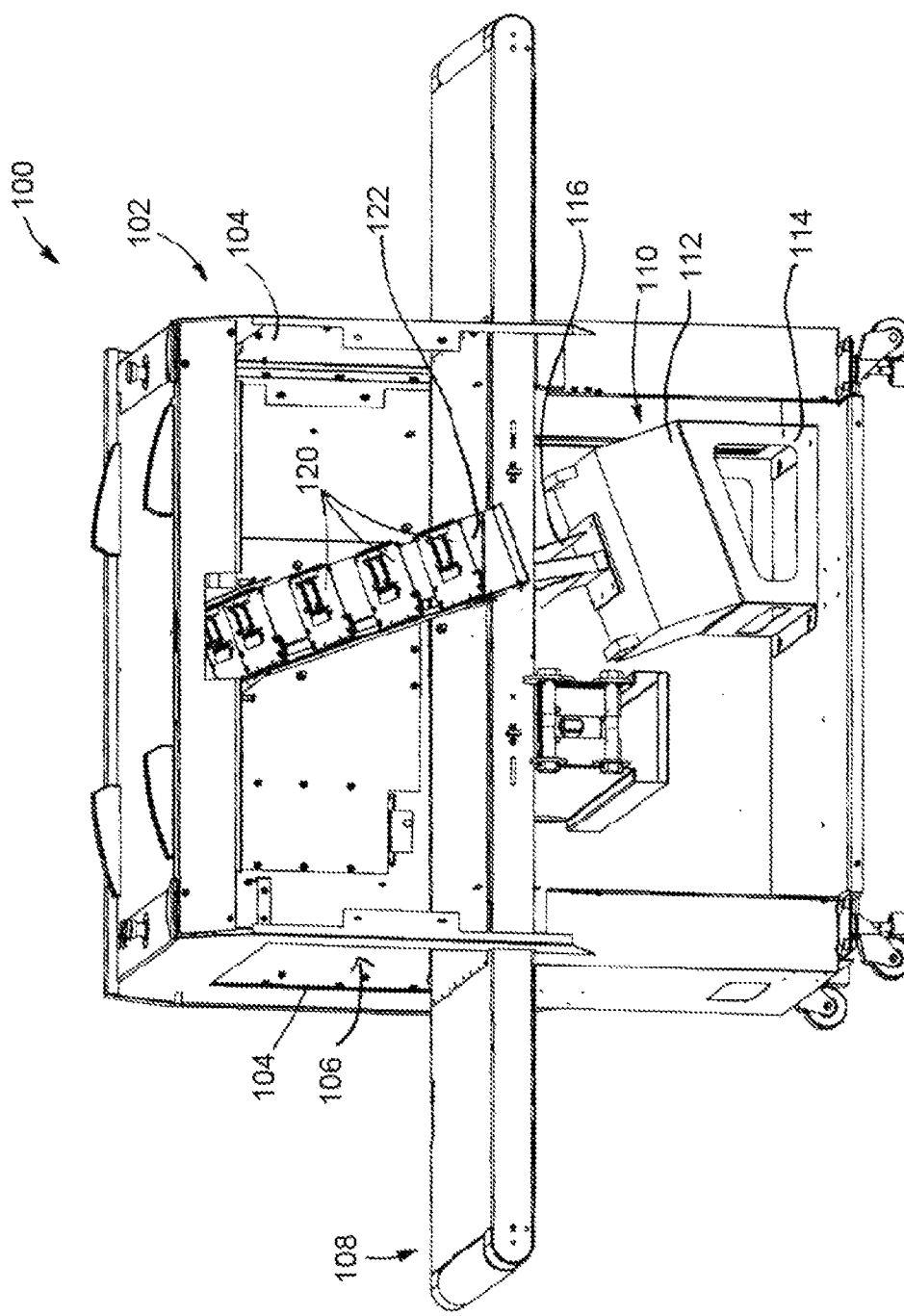
FIG. 1 is an illustration of an exemplary x-ray scanning device which may be used in accordance with the invention.

According to the aspect shown in FIG. 1, there is provided an exemplary x-ray scanning device 100. The x-ray scanning device 100 includes a housing 102 having openings 104 at either end thereof. The openings 104 provide access to a scanning chamber 106 passing through the housing 102. The system 100 may further include a displacement assembly 108, such as a conveyor, which extends through the scanning chamber 106 and which may be used to displace at least one object of interest to be scanned using the x-ray scanning device 100. The x-ray scanning device 100 further includes a source assembly 110. The source assembly 110 includes a source (not shown) for emitting electromagnetic radiation such as x-rays, a source assembly housing 112 at least partially enclosing the source, a pedestal 114 to which the source assembly housing 112 is mounted and a collimator 116 mounted to the source assembly housing 112 for directing x-rays emitted from the source. Collimator 116 may for example be a fan-shaped collimator for directing the x-rays in a fan-shaped beam. However, collimator 116 may be of any suitable shape and not only fan-shaped.

The x-ray scanning device 100 may further include a group of detectors including at least one detector 120 and preferably a plurality of detectors 120 each mounted to the bracket 122. In one aspect, the bracket is an L-shaped bracket which is positioned within the scanning chamber 106 such that the plurality of detectors 120 are mounted at least partially about the scanning chamber 106. In the aspect shown in FIG. 1 there is shown mounted within the scanning chamber a single bracket 122. In other aspects, the scanning chamber may include more than one bracket positioned within the scanning chamber and that the brackets do not have to have same orientation or angular position. It should be further understood that the bracket 122 does not have to be L-shaped. Rather, the bracket 122 may be linear or arc shaped or any other suitable shape.

In some embodiments, each detector 120 includes a detector card having a center point and edges. The center point corresponds to the geometric center of the detector cards. The edges of each detector card define the boundaries of the detector 120.

Figure 2:
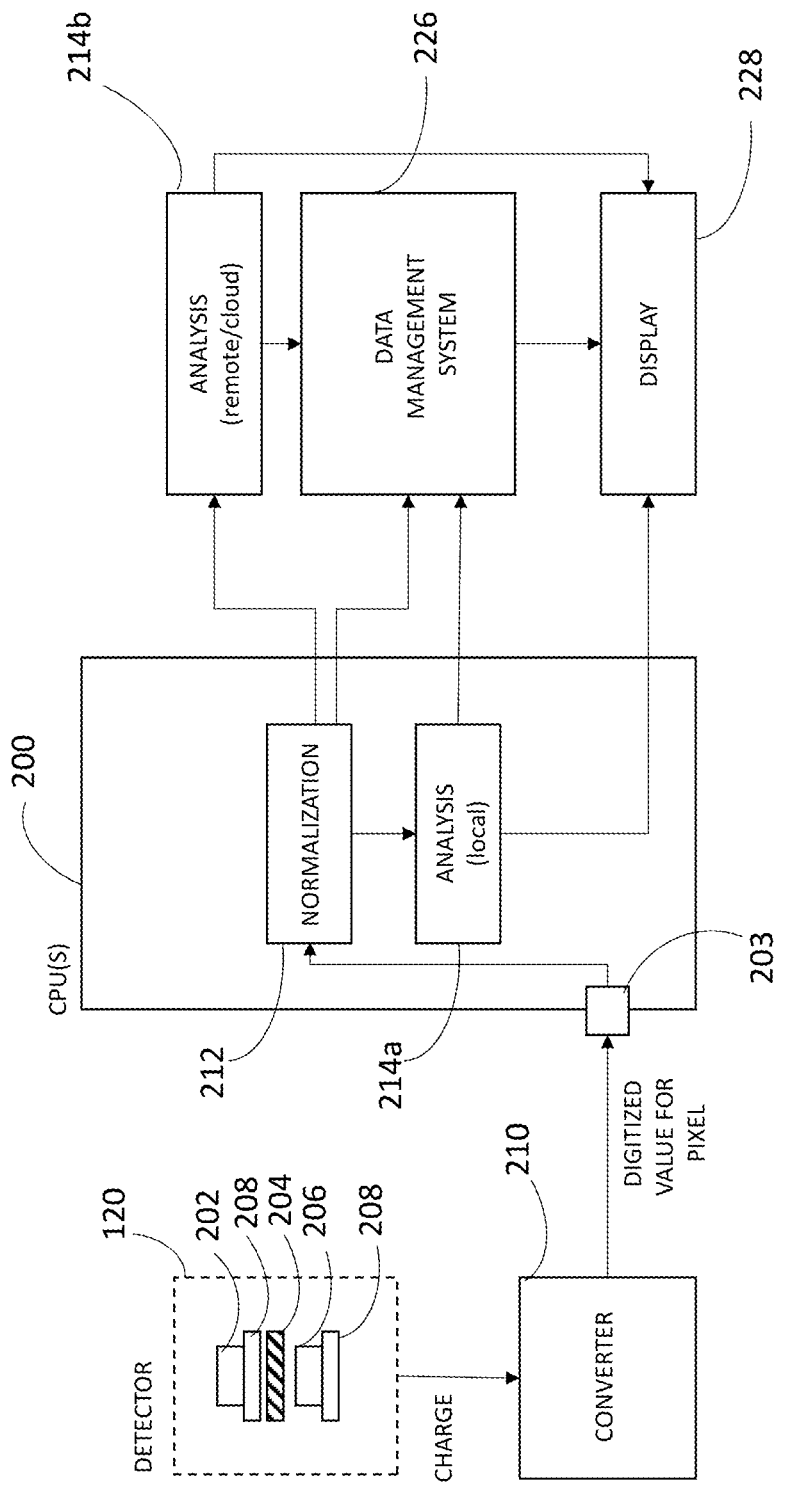
FIG. 2 is a diagram representation of a system which may be used in one aspect of the invention.

As shown in FIG. 2, each detector 120 may comprise a first scintillator 202, a filter 204 and a second scintillator 206. All of these may be sandwiched together as shown in FIG. 2 or may be otherwise suitably arranged. In a scanning operation, broad-spectrum x-rays are emitted by the source and are directed by the collimator 116 toward the plurality of detectors 120 within the scanning chamber 106. In the case of each detector 120, a plurality of the emitted x-rays encounters the first scintillator 202 which may be configured to detect the lower portion of the emitted x-ray signal spectrum. Residual low energy x-ray signals may then be stopped by the filter 204 and remaining x-ray signals from the emitted x-rays reach the second scintillator 206 which may be configured to detect a higher portion of the x-ray signal spectrum.

With further reference to FIG. 2, in one aspect, each of the scintillators 202, 206 converts the detected x-ray energy to light. Each of these scintillators 202, 206 is coupled with a photodiode 208 which captures the light from the respective scintillator 202, 206 and generates a corresponding analog electric signal, such as a photo current signal. The electric signal is further digitized by a converter 210. The digitized signal value is associated with a pixel of an image for providing a visual representation of a portion of an object within the scanning volume being scanned. The detectors thus measure to what degree the x-ray signal has attenuated due to passing through a defined inspection volume.

In the conversion of the light into an electric signal by the photodiodes 208, some uncertainties may be introduced in that a given light source may result in different electric signals since every detector card reacts slightly differently to the presence or absence of the electromagnetic radiation of an x-ray. In order to correct these variations and for the final image to appear more homogenously, each pixel of the image may be normalized by correcting an offset and gain in the light conversion. Such a normalization procedure may be executed for example using a normalization module 212 as shown in FIG. 2 in order to compensate for slight variations in offset and gain for each detector, as well as for estimating the expected uncertainties in the low-energy and high-energy signals and/or attenuation for each detector.

Detectors 120 and the x-ray scanning device 100 may be linked to one or more local central processing units (CPU) 200 or other local processing device coupled with the x-ray scanning device 100 via a suitable communication means such as input port 203. Thereby, x-ray signals detected by the detectors 120 may be analyzed locally using, for example, analysis module 214a. The information output from the analysis module 214a may be output locally. Such output may include output of an image to a display 228 for review by security personnel or to a suitable data storage volume, database or preferably data management system 226. Alternatively, the CPU may be configured to provide the x-ray scanning data to a remote location or cloud system for remote analysis 214b, via a suitable communication means, such as a network connection, for processing and may be further configured to receive from the remote location 214b the processed information sent back to the x-ray scanning device or a computer or monitor operably coupled therewith.

The detected x-ray energy signals resulting from the steps described above, once digitized, provide one or more data sets which can be displayed in graphical form and can be recognized by a human technician as indicating the presence of particular structures representing a specific class of objects or materials in the object. However, in an automatic method, the data must be evaluated by one or more computer processors processing the data.

Figure 3:
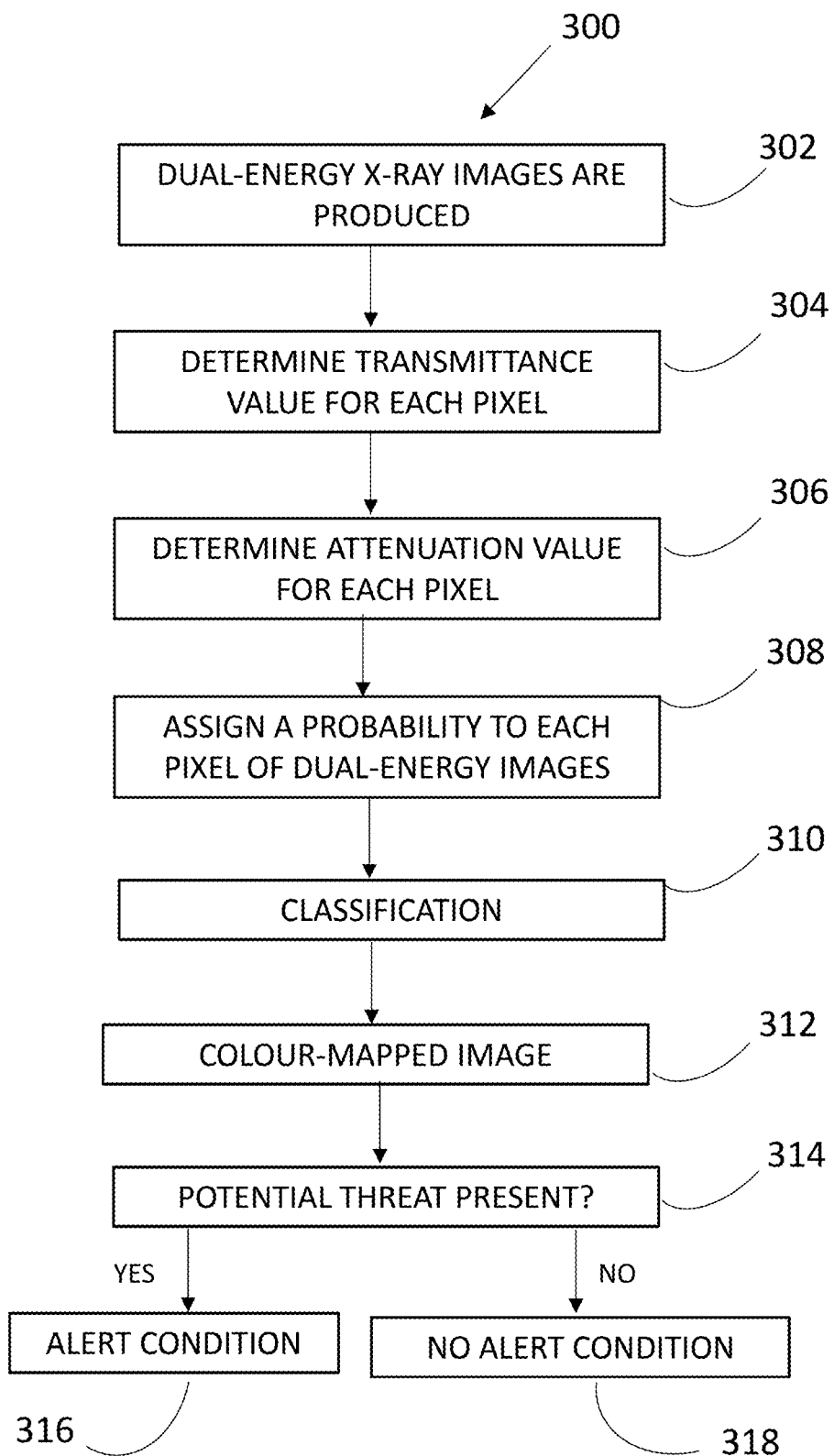
FIG. 3 is a flow chart diagram of the operational process according to one aspect of the invention.

FIG. 3 is a flowchart summarizing the operational process 300 of one aspect of the invention. In a first step 302, at least one x-ray image, composed of unprocessed or raw data, is produced. The at least raw data one x-ray image may include, for example, a set of dual-energy x-ray images. In one aspect, such raw data images may be retrieved from a suitable data storage medium, such as an archive or library of dual-energy x-ray images. In another aspect, the images may be produced de novo by performing a dual-energy x-ray scanning operation on an object using an x-ray scanning machine that produces raw data dual-energy x-ray scan images, for example, in the manner described above with reference to FIG. 1 and FIG. 2.

In a preferred aspect, the raw data image inputs for the neural network are expressed according to an attenuation scale. At step 304, the transmittance value of each pixel in the raw data x-ray images is determined. In one aspect, the transmittance value of a pixel may be determined from the corresponding raw detector pixel signal. Attenuation values are determined using the transmittance values of each pixel, as at step 306. The determination of attenuation values for each pixel from the corresponding transmittance values may be accomplished by any suitable means, but preferably by applying a logarithmic transformation and affine transformation to the subject transmittance value. Once the attenuation values for each pixel are determined, then the raw data x-ray images may be input into a neural network according to an attenuation scale for probabilistic analysis, as at step 308.

Probabilistic analysis is performed on the raw data image on a pixel-by-pixel basis to associate each pixel with a class label. As an example, such class labels may include "threat" or "not a threat" or the like. This analysis is performed using a neural network which, in one preferred aspect, is a convolutional neural network (CNN). Pixels which are adjacent or connected and which receive the same classification from the neural network form an object. The raw data for input is subject to no processing or very limited processing to normalize images from different scanners. The raw data images are not false colour images, as in other systems. Preferably, the raw dual-energy image is input to the CNN in patches. Patch overlap is ideally above the size of the largest expected potential threat object to be detected. For example, CD-ROMs have a large footprint, but poor attenuation. Accordingly, patches which are too small may result in false negatives.

In this preferred aspect, the purpose is to distinguish between detected objects which may pose a threat and should be investigated further, and those which are unlikely to pose a threat and do not necessarily require further investigation. This distinction may be made based on a threshold probability value, which may be predetermined. At step 308 a probability value is assigned to each pixel on the basis of the probabilistic analysis of the raw data x-ray image, expressed according to an attenuation scale, input into the neural network. The assignment of probability values to each pixel may be provided in a probability map. At step 310, pixels are classified according to the probability assigned by the neural network and the threshold probability value. Pixels having a probability value which exceeds the threshold probability value may be classified in a first classification. Pixels having a probability value which is below the threshold probability value may be classified in a second classification. As an example, the first classification may indicate that the pixel is likely associated with a potential threat and the second classification may indicate that the pixel is not likely to be associated with a potential threat. The threshold can be automatically determined by the network after the training process. Alternatively, the threshold can be predetermined or assigned by the operator in advance of the real-time object scanning.

As shown at step 312, the output may include a colour-mapped image wherein pixels representing potential threat objects are in one colour, such as red, and pixels representing non-threat objects are in another colour, such as blue. Since pixels making up the same object are grouped and classed together by the CNN, the objects in the output image may be easily distinguishable to an operator by the difference in colour. Preferably, the colour scheme may include flashing violet hues and shifted luma. Regions of interest may be further identified or made apparent by fitting rectangles on sets of connected pixels in the image.

The colour mapped image may be transmitted over a wide area network (WAN) in real-time or non-real-time. The image may be compressed using lossy compression, with lossiness knob set to adjust the detection performance impact against the detection latency (and scanning throughput). The scanning device runs as an HTTP service which can be hosted on-premises or in the cloud. To improve detector performance, the system may include an online feedback loop which allows for operators to flag false positives or false negatives which may then be used as inputs to the neural network to improve performance.

The input of the neural network is preferably a raw data dual-energy image with values expressed in an attenuation scale. For example, on such an attenuation scale, 0 could represent no attenuation and 1 could represent maximum attenuation (ie. Epsilon transmittance). The attenuation value of a pixel is more linear than its corresponding transmittance value because the signal at least generally follows the Beer-Lambert law. This makes the convolutional neural network (CNN) less sensitive to the "attenuation context" in which an object of a certain "relative attenuation" is present. Further, operation of the neural network using attenuation as input is more efficient since, in that case, the neural network does not have to be trained using, or "learn", a significant non-linearity.

Potential threat objects may include, for example, a potentially dangerous object, such as a weapon, drugs, contraband or potentially toxic or explosive materials or devices. If the presence of a potential threat object is probable at step 314, then an alert condition may be raised, as at step 316, to notify one or more operators that subsequent action is required. If the presence of a potential threat object is improbable at step 314, then no alert condition is raised, as at step 318.

In a preferred aspect, the analysis or classification of the raw dual-energy x-ray image data is performed automatically and preferably in real-time or near real-time using the probabilistic image analysis technique described herein in which a plurality of input data points, obtained from the raw dual-energy x-ray scan image data, contributes to the determination of the presence of a potential threat object. Although probabilistic classification techniques can include explicit, identifiable rules created by a programmer, a classification procedure that incorporates the results of training is preferred. For example, a classification algorithm can be used to process a training set consisting of patterns for structures of known classification. The results of this processing are used to adjust the algorithm, so that the classification accuracy improves as the algorithm learns by processing the training sets.

Trainable classifiers, such as the neural networks described herein within the context of the present invention, classify each pixel of the image into one of a plurality of classes. Artificial neural networks are used to perform pattern recognition and data classification tasks. Neural networks are fine grain parallel processing architectures composed of non-linear processing units, known as neurons or nodes. The neural network passes a signal by links from input nodes to output nodes. In some cases, such as with a feed-forward neural network, passing of the signal is in one direction only. A CNN includes at least one convolutional layer wherein the outputs of two or more other layers may be convolved and output as input to the next layer. In most implementations, the nodes are organized into multiple layers: the input layer, output layer, and several intermediate or "hidden layers" in between. Each hidden layer successively applies a filter or performs an operation on the input data.

In order to perform semantic segmentation, the algorithm must determine the classification of each of the pixels and determine which pixels correspond to the same object. As is described in more detail hereinbelow, neural networks suitable for semantic segmentations, such as CNNs, and more specifically FC-Densenet, can be trained by inputting new raw dual-energy x-ray scan images of known objects or images retrieved from a library or archive of images saved in a data management system or on a data storage medium. The training images may be pre-labeled manually or automatically prior to inputting to the network so that the neural network can make an appropriate association between the output with the input.

Figure 4:
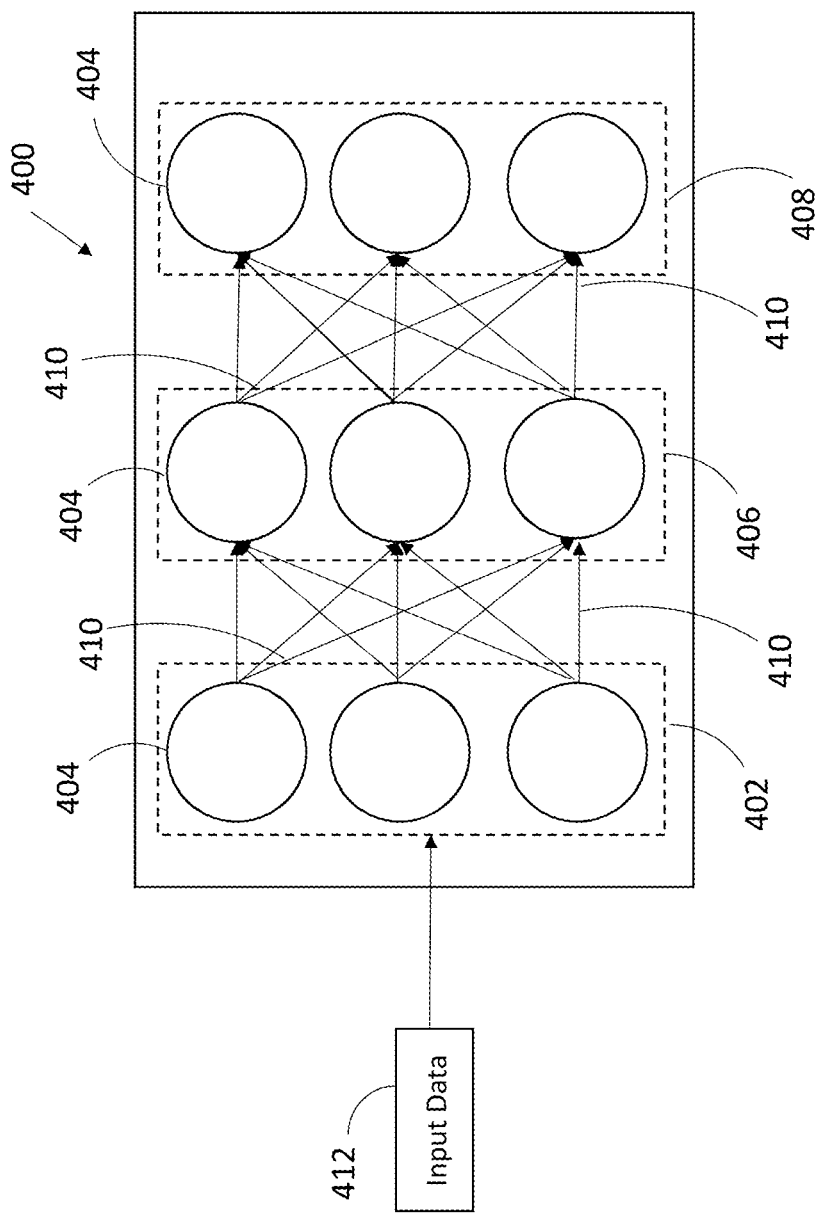
FIG. 4 is a diagram representation of an artificial neural network as may be used in accordance with the invention; and, FIG. 5 is a diagram representation of the training process for the artificial neural network according to one aspect of the invention.

For illustration of the general architecture of a basic neural network, there is provided in FIG. 4 a schematic representation of an artificial neural network 400 network consisting of an input layer 402 of neurons or nodes 404, at least one hidden layer 406, and an output layer 408. The neuron layers are linked via a set of synaptic interconnections 410. Each neuron 404 in the input layer 402 is typically connected to each neuron 404 in the hidden layer 406, and each neuron 404 in the hidden layer 406 is typically connected to each neuron 404 in the output layer 408, via a synaptic connection 410. Connections 410 between nodes may be physical, electronic hardware connections, or they may be embodied in software, as may be the neurons 404 themselves, which software operates on computers.

The neurons or nodes in a neural network typically accept several inputs as a weighted sum (a vector dot product). This sum is then tested against an activation function, which is typically a threshold, and then is processed through an output function. In artificial neural networks, the activation function may also be referred to as a "transfer function". The activation function of a node defines the output of that node given an input or a set of inputs. The inputs for the nodes comprising the input layer come from external sources, such as input data. The inputs for the nodes comprising the intermediate or hidden layers are the outputs from the nodes of the input layer, for the first hidden layer, or from preceding hidden layers in the neural network. The inputs for the nodes comprising the output layer are the outputs from the last hidden layer in the neural network. The output function could be a non-linear function such as a hard-limiter, a sigmoid function, a convolution, a sine-function or any other suitable function known to a person of ordinary skill in the art.

The activation function threshold determines how high the input to that node must be in order to generate a positive output of that node. For example, a node may be considered to be turned "ON" whenever its value is above a predetermined value such as, for instance, 0.8 and turned "OFF" with a value of less than another value such as 0.25. The node may have an undefined "maybe" state between those values. Between two layers, multiple node connection patterns are possible. In a fully interconnected network, every node in one layer is connected to every node in the next layer. "Pooling" is another arrangement wherein multiple nodes in one layer may connect to a single node in the next layer. This allows for a reduction in the number of neurons in a subsequent layer. Other arrangements are possible.

The connectivity pattern between any two layers defines which node receives the output value of one or more previous nodes as their input. Each connection between nodes is assigned a weight that represents its relative importance. The relative importance is determined by training the neural network, which is discussed hereinafter. A propagation function computes the input to a neuron from the outputs of its predecessor nodes and the strength of their connections. The connection between two nodes is thus realized in mathematical terms by multiplying the output of the one or more lower level nodes by the strength of that connection (weight). At each instant of propagation, the values for the inputs define an activity state. The initial activity state is defined upon presentation of the inputs to the network.

The output response of any hidden layer node and any output layer node is a function of the network input to that node defined by the difference of the threshold of that node and the input to it. The value of the input into each hidden or output layer node is weighted with the weight stored for the connection strengths between each of the input and hidden layer nodes, and the hidden and output layer nodes, respectively. Summing over all connections into a particular node and subtracting this sum from the threshold value may be performed according to sigmoid-type functions, sine-type functions, or any other suitable function known in the art that may be used to obtain the desired type of response function for the output of a node. The weights are chosen to minimize the error between the produced result and the correct result. A learning rule defines how to choose the weight values and adjust them with subsequent instances of training. Several commonly used learning rules are back-propagation, competitive learning, adaptive resonance, reinforcement learning, supervised learning, unsupervised learning and self-organization, though other learning rules may be relied upon within the context of the present invention.

In a preferred aspect, the artificial neural network uses back-propagation learning. The back-propagation learning algorithm is derived from the chain rule for partial derivatives and provides a gradient descent learning method in the space of weights. Back-propagation learning is a supervised learning method. The purpose for back-propagation learning is to find a function that best maps a set of inputs to their correct output. Accordingly, back-propagation learning involves a set of pairs of input and output vectors. The artificial neural network uses an input vector to generate its own, or actual, output vector. The actual output vector is compared with a desired output, or target, vector. The target vector may be defined in the course of training but correlates with the input vector. During the back-propagation training process, the connection weights are adjusted iteratively to best map the target vector and the actual output vector. The conventional delta rule may be used for this calculation where the weight for a particular synapse or connection between nodes is adjusted proportionally to the product of an error signal, delta, available to the node receiving input via the connection and the output of the node sending a signal via the connection. If a node is an output node, the error signal is proportional to the difference between the actual and target value of the node. If it is a hidden layer, it is determined recursively in terms of the error signals of the nodes to which it directly connects and the weights of those connections.

Thus, the training of a neural network is the process of setting the connection weights so that the network produces a desired output in response to any input that is normal for the situation. Supervised training refers to training which requires a training set, i.e. a set of input-target output patterns. The back-propagation algorithm is an efficient technique to train some types of neural network. It operates to send an error back through the neural network during the training process, thereby adjusting all the node connection weights in correspondence with their contribution to the error. The weights of the network therefore gradually drift to a set of values which better maps the input vector with the correct or target output vector. The initial weights may be chosen randomly, within reasonable limits, and adjustments are left to the training process.

The artificial neural network 400 of FIG. 4 is preferably trained on a suitably large set of dual-energy x-ray scan images composed of raw data or values calculated from raw data, such as transmittance or attenuation. The set of images includes images of objects of different shapes and composed of different materials scanned at various angles and orientations. The set of images will include images of objects which may or may not be potentially harmful. Such a set of images, for example, may be generated by new x-ray scans of objects or may be retrieved from a library or archive of images saved in a data management system or on a data storage medium. The images in the training data set must be labeled or tagged to identify the contents of the image including the names and positions of objects or materials. This labeled raw scan data is used as an input-set to be used for training the neural network. In this context, the labeled raw scan data becomes "training data". The training data is input to the neural network to generate an output 408, in accordance with the error back-propagation learning method described above. Thus, the input data 412 to be used to train the neural network 400 preferably includes dual-energy x-ray images composed of raw signals, expressed according to an attenuation scale The purpose of training the neural network is to have a processing means capable of recognizing a signature representing an object or material of interest, particularly if the material or object is potentially harmful. This signature is defined as an array of numbers corresponding, on a one-to-one basis, to the discretized values of a physical quantity, such as the energy of X-rays, and could include unrelated, but relevant, other values, such as transmission detector array data, position and volume of the scanned object in the x-ray scanning machine, and other environmental factors. The array may consist of any amount of data points.

The training process is repeated using labeled scan data of a sufficiently large number of raw data dual energy images containing objects and materials of interest in a variety of permutations and combinations to model real-world scenarios. Since the training data is obtained by scanning objects having known configuration and including known materials, each output data during the training process may be further labeled or tagged to identify whether the respective training data represents a defined or known object or material of interest. This output data of the training step may be further stored in a suitable library, data management system or database such a file server on a digital computer system along with the tagged identification information. Furthermore, the library, data management system or database of training data may be enhanced to incorporate and reflect all previously known objects or materials of interest, including threat materials or objects or potentially harmful materials or objects, and their corresponding raw dual-energy x-ray scan data.

Figure 5:
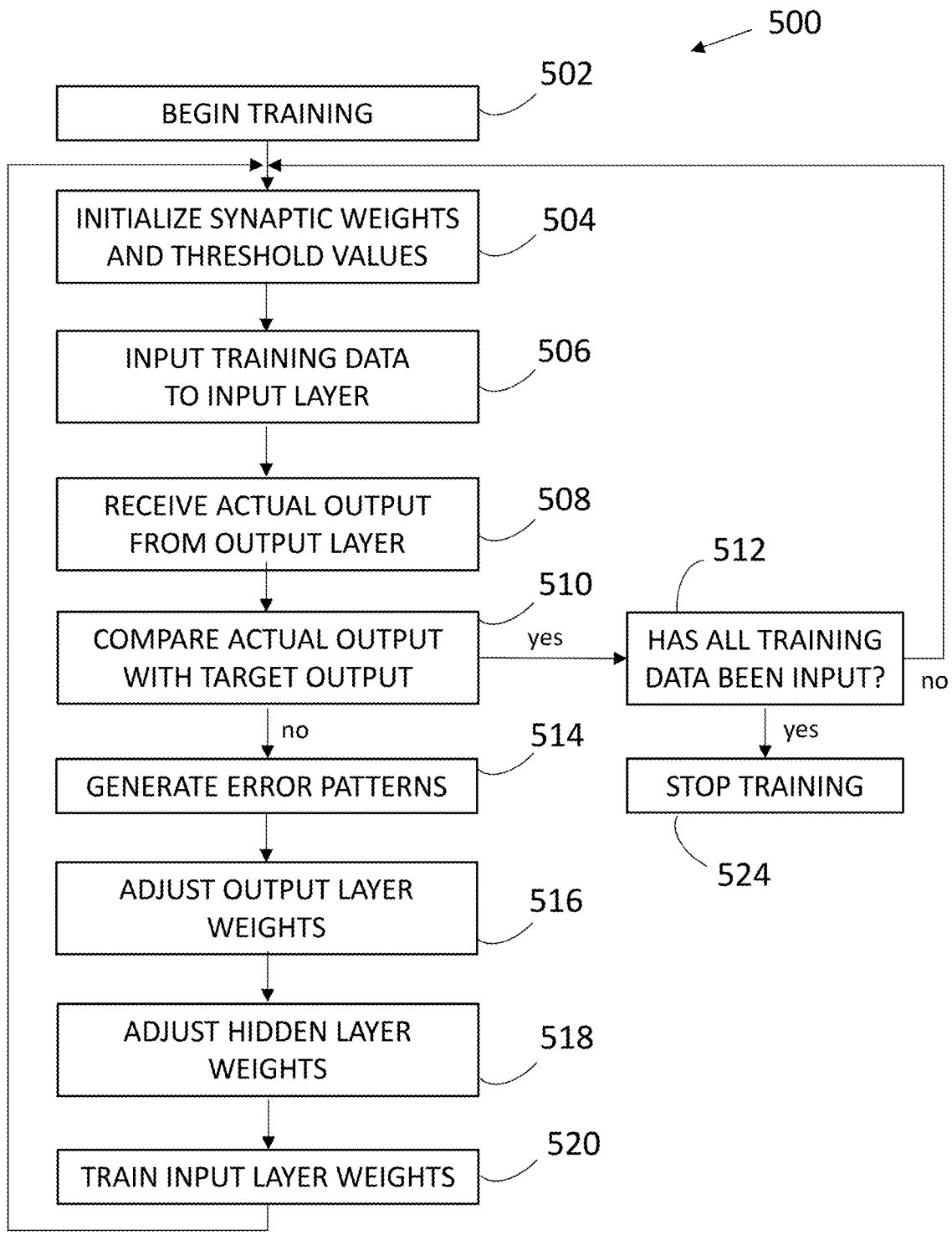

FIG. 5 is a flow diagram of the back-propagation training process 500 for an artificial neural network, in accordance with one aspect of the invention. One of ordinary skill in the art would appreciate that the processing is conducted using one or more computers having a plurality of processors and system architecture for executing the machine learning analytical processes described herein, embodied in at least one software program, a plurality of storage devices or a data management system for storing the requisite data, library information, and other information necessary to conduct these analyses, and at least one output device, such as one or more other computing devices, servers or data management systems, networks, "cloud" systems, monitors or other computing devices and peripherals. It should also be understood that the software including the neural network may be housed on a computer system or data management system at a remote location from the x-ray scanning device. X-ray imaging data produced by the scanning device may be sent via a suitable network connection to the remote computer system or data management system for processing. The output of the neural network may then be sent back to the location of the x-ray scanning device for review by an operator.

At the beginning of the training process 502, the synaptic weights and thresholds of the neural network are initialized 504 with, for example, random or arbitrary numbers that are within reason to a person skilled in the art. After initialization 504, the input layer of the neural network is introduced 506 to a first set of training data and the neural network is run to receive 508 an actual output. The neural network makes use of the randomly assigned weights and thresholds to generate at least one output based on a suitable resolving function, as described above. The outputs may, for example, be in the form of differentiable signals such as numerals between, 0 and 1, in the form of positive or negative states implied by an output numeral of greater than or less than 0 respectively, or any other suitable indication as evident to a person of ordinary skill in the art. One form the outputs may take in accordance with the present invention includes one or more values between 0 and 1 indicating a probability as to the presence of an object or material of interest in an image, such as an object which constitutes a potential threat. As previously mentioned, the output may include a colour-mapped image to be shown to an operator wherein potential threat objects and non-threat objects are shown in different colours.

The first set of training data is introduced into the system and, based on the random weights and thresholds, produces an actual output, such as, for example, a numeral greater than 0. If the training data represents an object or material of interest, this output indication is set as a benchmark to identify an object or material of interest while, for example, a numeral less than 0 may be set to identify an object or material that is not of interest. Once a suitable benchmark is set, the training process is repeated with the next set of training data and corresponding actual outputs are received. At step 510, the actual output is compared with the desired or target output, defined by an operator with knowledge as to whether input data is or is not representative of an object or material of interest, for the corresponding set of training data that was input to the neural network in step 506. If the actual output is commensurate with the desired or target output or, if the difference between the target and actual output falls below a predefined acceptable level, a check 512 is made to determine whether the neural network has been trained on the entire set of training data. If not, then the next set of training data is introduced to the neural network at step 506 and the foregoing steps 502 to 510 are repeated. The training process 500 continues until the neural network has been trained on the entire set of training data.

If the comparison 510 suggests that the actual output is not in agreement with the desired or targeted output, the ensuing additional steps are performed. At step 514, the difference between the actual output and the target output is used to generate an error pattern in accordance with a suitable back-propagation rule such as the 'delta rule' or any other error estimation rule known to a person of ordinary skill in the art. The error pattern is used to adjust, at step 516, the synaptic weights of the output layer such that the error pattern would be reduced at the next instance the training process 500 is performed, if the same set of training data were presented as the input data. Then, at step 518, the synaptic weights of the hidden layers, preceding the output layer, are adjusted by comparing the hidden layer node actual outputs with the results of nodes in the output layer to form an error pattern for the hidden layer.

The error can thus be propagated as far back over as many hidden layers as are present in the artificial neural network. Finally, the weights for the input layer are similarly adjusted at step 520, and the next set of training data is introduced to the neural network to iterate through the learning cycle again. The neural network is therefore trained by presenting each set of training data in turn at the inputs and propagating forwards and backwards, followed by the next input data, and repeating this cycle a sufficient number of times such that the neural network iteratively adjusts the weights of the synaptic connections between layers to establish a set of weights and thresholds which may be relied upon to produce a pattern of actual output that is in agreement with the target output for the presented input data. Once the desired set of weights and thresholds is established, preferably when all training data has been input to the neural network, then the learning process may be terminated, as shown at step 524. The learned information of a neural network is contained in the values of the set of weights and thresholds.

Once the neural network has been trained using the training data, then recognition and classification of pixels representing objects in an image may be performed using live input data. Live input data may be provided from stored or archived scan images or may be provided by performing new scans using an x-ray scanning device such as the one described above with reference to FIG. 1 and FIG. 2. Depending on the input data, filters may be applied, or specific operations performed, in order to achieve the best performance from the neural network for the live input data. The output of the neural network may be used to modify the display provided by an operator in a manner which would draw the attention of the operator to a specific object or material automatically and in real-time or in near-real-time. The operator may then subsequently raise an alert condition if the object or material of interest identified by the neural network constitutes a potentially harmful object or material. In another aspect, the alert condition may be automatically initiated based on the output of the neural network.

It should be further understood that the training operation can be performed on one machine and the results can be replicated in additional machines. For example, training of a neural network results in a set of weight values defining the association between nodes of the neural network. This set can be recorded and incorporated in other, similar neural networks.

The present disclosure is in the context of probabilistic analysis of raw or unprocessed data in the form of x-ray scan images as produced by transmission x-ray scanning devices, preferably using dual-energy channels for inspection. The present disclosure would also apply to other forms data which may be extracted from an inspected object. Such other forms of data may include images provided by multi-channel x-ray scans, trace material detection, millimeter wave scans, spectral analysis, x-ray diffraction information, x-ray backscatter images and any other means of inspection for extracting data suitable for analyzing the physical or chemical properties of an object or volume subject to inspection. It should be further understood that the extracted data use for analysis may be unprocessed or processed data.

While the invention has been described in terms of specific embodiments, it is apparent that other forms could be adopted by one skilled in the art. For example, the methods described herein could be performed in a manner which differs from the embodiments described herein. The steps of each method could be performed using similar steps or steps producing the same result, but which are not necessarily equivalent to the steps described herein. Some steps may also be performed in different order to obtain the same result. Similarly, the apparatuses and systems described herein could differ in appearance and construction from the embodiments described herein, the functions of each component of the apparatus could be performed by components of different construction but capable of a similar though not necessarily equivalent function, and appropriate materials could be substituted for those noted. Accordingly, it should be understood that the invention is not limited to the specific embodiments described herein. It should also be understood that the phraseology and terminology employed above are for the purpose of disclosing the illustrated embodiments, and do not necessarily serve as limitations to the scope of the invention.

What is claimed is:

1. A method for detecting at least one object of interest in at least one raw data x-ray image, the method comprising the steps of:
    emitting an incident x-ray radiation beam through a scanning volume having an object therein;
    detecting x-ray signals transmitted through at least one of the scanning volume and the object;
    deriving the at least one raw data x-ray image from the detected x-ray signals;
    inputting the raw data x-ray image, expressed according to an attenuation scale, into a neural network;
    for each pixel in the raw data x-ray image, outputting from the neural network a probability value assigned to that pixel, wherein the probability value is indicative of whether the pixel is likely associated, or not likely associated, with a potential threat; and,
    classifying each pixel in the raw data x-ray image into at least one of a first classification or second classification based on whether the probability value associated with the pixel exceeds, or does not exceed, a predetermined threshold probability value.

2. The method of claim 1, wherein the step of inputting the raw data x-ray image expressed according to an attenuation scale further comprises the steps of:
    determining a transmittance value for each pixel in the raw data x-ray image; and,
    determining an attenuation value from each transmittance value.

3. The method of claim 1, wherein the outputting step outputs a probability map for each pixel in the raw data x-ray image.

4. The method of claim 3, wherein the method further comprises: providing a colour-mapped image based on the probability map showing pixels classified in the first classification in a first colour scheme and pixels classified in the second classification in a second colour scheme.

5. The method of claim 4, wherein the first colour scheme and the second colour scheme at least one of flashes, shifts hue and shifts luma.

6. The method of claim 1, wherein the classifying step is by way of semantic segmentation.

7. The method of claim 1, wherein the neural network is a convolutional neural network.

8. The method of claim 7, wherein the convolutional neural network is a FC-Densenet.

9. The method of claim 1, wherein the at least one raw data x-ray image includes a set of raw data dual-energy x-ray images.

10. A system for detecting at least one object of interest in at least one raw data x-ray image, comprising:
    an x-ray emitter for emitting an incident x-ray radiation beam through a scanning volume having an object therein;
    at least one detector for detecting x-ray signals transmitted through at least one of the scanning volume and the object;
    at least one processor for deriving at least one raw data x-ray image from the detected x-ray signal;
    at least one processor configured to:
        input the raw data x-ray image, expressed according to an attenuation scale, into a neural network;
        output from the neural network a probability value assigned to each pixel in the raw data x-ray image, wherein the probability value is indicative of whether the pixel is likely associated, or not likely associated, with a potential threat; and,
        classify each pixel in the raw data x-ray image into at least one of a first classification or second classification based on whether the probability value associated with the pixel exceeds, or does not exceed, a predetermined threshold probability value.

11. The system of claim 10, wherein to express the raw data x-ray image according to an attenuation scale, the at least one processor is further configured to:
    determine a transmittance value for each pixel in the raw data x-ray image; and,
    determine an attenuation value from each transmittance value.

12. The system of claim 10, wherein to output the probability value assigned to each pixel in the raw data x-ray image, the at least one processor is further configured to output a probability map for each pixel in the raw data x-ray image.

13. The system of claim 12 wherein the at least one processor is further configured to provide a colour-mapped image showing pixels in the first classification in a first colour scheme and pixels in the second classification in a second colour scheme.

14. The system of claim 13, wherein the first colour scheme and the second colour scheme at least one of flashes, shifts hue and shifts luma.

15. The system of claim 10, wherein the neural network is configured to classify each pixel in the raw data x-ray image by way of semantic segmentation.

16. The system of claim 10, wherein the neural network is a convolutional neural network.

17. The system of claim 16, wherein the convolutional neural network is a FC-Densenet.

\* \* \* \* \*